United States Patent
Rigaux et al.

(10) Patent No.: US 8,428,734 B2
(45) Date of Patent: Apr. 23, 2013

(54) DEVICE FOR THE ELECTROTHERAPEUTIC TREATMENT OF TENSION HEADACHES

(75) Inventors: Pierre Rigaux, Liege (BE); Pierre-Yves Muller, Geneva (CH)

(73) Assignee: STX-Med Sprl, Angleur Liège (BE)

( * ) Notice: Subject to any disclaimer, the term of this patent is extended or adjusted under 35 U.S.C. 154(b) by 769 days.

(21) Appl. No.: 12/359,716

(22) Filed: Jan. 26, 2009

(65) Prior Publication Data

US 2009/0210028 A1    Aug. 20, 2009

(30) Foreign Application Priority Data

Feb. 20, 2008  (EP) ..................................... 08447012

(51) Int. Cl.
*A61N 1/18* (2006.01)

(52) U.S. Cl.
USPC .............. 607/46; 607/139; 607/140; 607/141

(58) Field of Classification Search .................... 607/46, 607/139–141
See application file for complete search history.

(56) References Cited

U.S. PATENT DOCUMENTS

| | | | |
|---|---|---|---|
| 3,746,004 A | 7/1973 | Jankelson | |
| 6,077,237 A * | 6/2000 | Campbell et al. | ............. 600/587 |
| 2002/0161416 A1 | 10/2002 | Huang | |
| 2007/0276451 A1 * | 11/2007 | Rigaux | ........................... 607/48 |

FOREIGN PATENT DOCUMENTS

| | | | |
|---|---|---|---|
| WO | WO 2006/051370 A1 | 5/2006 | |
| WO | WO 2006/063417 A1 | 6/2006 | |

OTHER PUBLICATIONS

Ahmed et al., "Use of the percutaneous electrical nerve stimulation (PENS) in the short-term management of headache," *Headache* (2000) 40: 311-315.

Farina et al., "Headache and cervical spine disorders: Classification and treatment with transcutaneous electrical nerve stimulation," *Headache* (1986) 26: 431-433.

Melzack et al., "Pain mechanisms: A new theory," *Science* (1965) 150: 971-979.

Solomon et al., "Treatment of headache by transcutaneous electrical stimulation," *Headache* (1985) 25: 12-15.

Wall et al., "Temporary abolition of pain in man," *Science* (1967) 150: 108-109.

Woolf et al., "Antinociceptiv effect of peripheral segmental electrical stimulation in the rat," *Pain* (1980) 8: 237-252.

Alon, G., "Chapter 3—Principles of Electrical Stimulation," *Clinical Electrotherapy* Appleton & Lange 1987: 29-47.

Instrumentation for Neuromuscular electrical stimulation, Snyder-Mackler L, Robinson Aj, eds.; *Clinical Electrophysiology*;. Baltimore, MD; Williams & Wilkins; 1989: 99.

Instrumentation for Neuromuscular electrical stimulation, Snyder-Mackler L, Robinson AJ, eds.; *Clinical Electrophysiology*;. Baltimore, MD; Williams & Wilkins; 1989: 100.

Principes Fondamentaux de l'électrostimulation, *Medi-Compex 1994*; Courant optimal; Durée de l'impulsion électrique rectangulaire, pp. 1.2.3 to 1.2.5.

Allais et al., "Non-pharmacological approaches to chronic headaches: transcutaneous electrical nerve stimulation, lasertherapy and acupuncture in transformed migraine treatment," *Neurol Sci* (2003) 24: S138-S142.

* cited by examiner

*Primary Examiner* — Joseph Dietrich
(74) *Attorney, Agent, or Firm* — Merchant & Gould P.C.

(57) ABSTRACT

A device is for the electrotherapeutic treatment of headaches such as tension headaches and migraines. An electrode support (10) has a shape and is size selected so as to allow, independently from the subject, the excitation of the afferent paths of the supratrochlear (2) and supraorbital (3) nerves of the ophthalmic branch (1) of the trigeminal nerve. An electrical circuit includes a programmable signal generator suitable for creating pulses of a duration of between 150 and 450 microseconds with a maximum increase in intensity of 0 to 20 milliamperes at a rate of less than or equal to 40 microamperes per second and with a step up in intensity not exceeding 50 microamperes.

4 Claims, 2 Drawing Sheets

DEVICE FOR THE ELECTROTHERAPEUTIC TREATMENT OF TENSION HEADACHES

Figure 1:
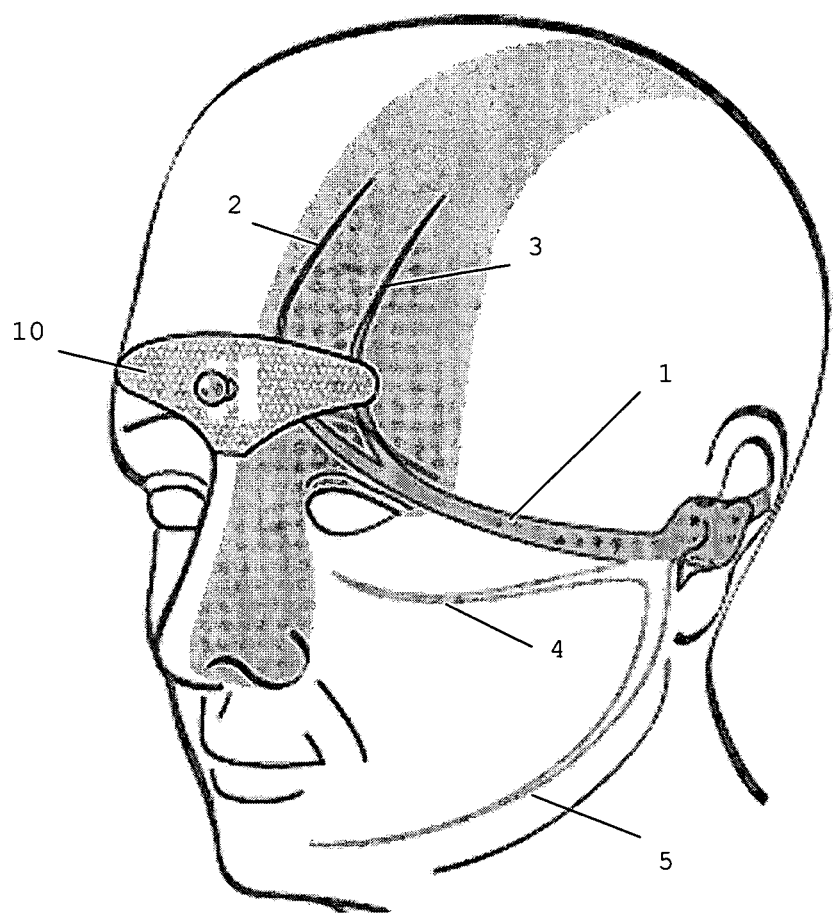

This application claims the benefit of Serial No. 08447012.9, filed Feb. 20, 2008 in the EPO and published as EP 2 092 951, which application is incorporated herein by reference. A claim of priority to the extent appropriate is made.

SUBJECT OF THE INVENTION

The present invention relates to an electrical device with electrodes applied to the upper half of the face and aimed at treating migraines and headaches.

TECHNOLOGICAL BACKGROUND AND STATE OF THE ART

One known analgesic electrotherapy technique is transcutaneous electrical nerve stimulation, commonly called TENS (the acronym). The latter consists in exciting sensitive afferent paths by means of electrodes placed on the skin, so as to lessen or block the pain (Gate control theory, stimulation of the production of endogenous analgesics). This technique is widely known [1,2,3] and regularly used to combat various types of pain.

Most migraines and tension headaches spread on to the surface of the front half of the cranium. The afferent path of this pain is located in the trigeminal nerve (*Trigeminus nervus*), shown in FIG. 1, which has three branches: the ophthalmic branch 1, the maxillary branch 4 and the mandibular branch 5. The afferent path of the above-mentioned pain is more precisely the upper branch of the trigeminal nerve 1 which is also called Willis' ophthalmic nerve.

This nerve divides into two branches on the forehead: the internal frontal (or supratrochlear) nerve 2 and the external frontal (or supraorbital) nerve 3.

Thus the application of analgesic electrotherapy of a TENS type to the supraorbital and supratrochlear nerves allows one to combat the pain of most migraines and tension headaches as described in the medical literature [4, 5, 6, 7].

International application WO 2006/063417 A1 belonging to the Applicant describes a device for electro-inhibition of the facial muscles marketed under the name of Safetox® Beauty, which applies electric currents via a bipolar electrode placed on the forehead. The two poles of the electrode are part of a single structure comprising a piece of cloth acting as a support. The electrodes are covered with a self-adhesive conductive gel on their inner surface which is intended to be in contact with the skin. They are in the form of two conductive silvered zones that impregnate the piece of cloth, which is therefore also conductive on its outer surface in contact with the electricity supply pads. This device is used without causing significant pain. This is possible because the electrode of said device has been designed to be of a very small size. Typically the two poles of the electrode have a maximum surface area of between 100 and 200 mm$^2$ and they are separated by a distance of 4 to 8 mm. The relevant surface of the periosteum is very small and the current does not penetrate the tissues very deeply.

Thanks to its limited surface area, this type of electrode allows an action only on the supratrochlear (internal frontal) nerves but has no effect on the supraorbital (external frontal) nerves. Therefore it does not entirely fulfil the criteria of effectiveness for an analgesic electrotherapy treatment of a TENS type in the case of migraines and headaches.

When a wider electrode of the usual form is used to excite the afferent paths of the supraorbital (external frontal) nerves, the currents generated by the Safetox® Beauty cause pains, which make the above-mentioned treatment unbearable.

Document WO 2006/051370 A1 relates to an electrotherapy device applied in particular to the treatment of migraines and other headaches, neuralgias, ophthalmic shingles, Arnold's syndrome etc. This is a device comprising at least one electrode for the application of a treatment current and a means of control. The latter comprises at least a means of activation for initiating the provision of a predetermined current profile in its various parameters, in particular the intensity, and a means of stabilisation which, when it is activated, causes a modification of said current profile by restricting the intensity of the current to its value at the moment of activation of said means of stabilisation. This would therefore limit the risk of too intense a pain for the patient during the application of a predetermined current profile thanks to the means of stabilisation that the patient himself can activate. The electrodes are four in number and associated laterally two by two, each path having one supraorbital frontal electrode and a zygomatic electrode. This arrangement corresponds to the surface projection of the trifurcation of the trigeminal nerve on the surface at the zygomatic position and the passage of its ophthalmic branch over the supraorbital ridge. The cloth electrode support comprises in particular a strip equipped with two sliding sleeves to allow the adjustment of the position of the electrodes at the level of the supraorbital ridges, which allows the specific morphological details of each patient to be taken into account.

TECHNICAL PROBLEM TO BE RESOLVED

The application of electrodes and current of a TENS type to the forehead to excite the afferent paths of the supraorbital and supratrochlear nerves thus produces pain that is difficult to bear. This pain explains why the TENS electrotherapy technique, although very popular, is very little used, if at all, in the treatment of migraines and headaches. In fact, patients cannot cope with the treatment, because the pain felt in the forehead is so intense.

The periosteum that covers the surface of the frontal bone is very densely innervated with nerve fibres that sense pain (nociceptive). The closeness of the surface of an electrode applied to the forehead and the periosteum of the frontal bone explains the activation of pain by electric pulses.

AIMS OF THE INVENTION

The present invention aims to provide a solution that allows in particular to solve the above-mentioned technical problem.

The present invention has therefore the aim of developing a form of electrode as well as of selecting electrical parameters such as the application of analgesic electrotherapy of the TENS type to the forehead in a way that is not only effective but also without pain for the patient and comfortable.

The present invention also aims to provide a system of electrodes which can easily be adapted to the morphology of the user.

MAIN CHARACTERISTIC ELEMENTS OF THE INVENTION

A first subject of the present invention relates to a device for the electrotherapeutic treatment of headaches such as tension headaches and migraines, comprising an elongated symmetrical element to support two contact electrodes to be applied transversally to the upper part of the face, in the intraorbital region, each of the electrodes being in contact with a self-adhesive conductive gel applied to the support surface which is intended to be applied to the skin of the face, said conductive gel being applied to two given lateral zones, mainly covering the entire support with the exception of an insulating central zone, as well as an electric circuit to supply said electrodes by means of low-voltage electric pulses, characterised in that:

the electrode support has a shape and size selected so as to allow, independently from the subject, the excitation of the afferent paths of the supratrochlear and supraorbital nerves of the ophthalmic branch of the trigeminal nerve;

the electric circuit comprises a programmable signal generator which is suitable for generating pulses of a duration of between 150 and 450 microseconds with a maximum increase in intensity from 0 to 20 milliamperes at a rate of less than or equal to 40 microamperes per second and with a step up in intensity not exceeding 50 microamperes.

According to a preferred embodiment of the invention, the electrode support has a central part of height H1 which is higher than the height H2 of each of the outer parts, the upper ends of the two outer parts being at a level slightly below the level of the central part, once the support is correctly positioned on the face.

As an advantage, the electrode support has in terms of dimensions:
a length or lateral extension L of between 70 and 115 mm;
a height of the central part H1 of between 15 and 50 mm;
a height of each of the outer parts H2 of between 5 and 20 mm.

As a particular advantage,
the length L has a value of about 95 mm;
the height of the central part H1 has a value of about 30 mm;
the height of each of the outer parts H2 has a value of about 10 mm.

As a further advantage, the duration of the pulses is about 250 microseconds.

As a further advantage, the step up in intensity is of about 30 microamperes.

In countries where such a method is patentable, a second subject of the invention concerns a therapeutic method of treatment for headaches such as tension headaches and migraines by means of the above-mentioned device, characterised at least by the following stages:

the self-adhesive electrode support is placed on the upper part of the face in the intraorbital region so as to cover on each side the afferent paths of the supratrochlear and supraorbital nerves of the ophthalmic branch of the trigeminal nerve;

by means of the programmable signal generator, an electrical signal is generated which comprises rectangular pulses of a duration of between 150 and 450 microseconds and preferably 250 microseconds, with a maximum increase in intensity of 0 to 20 milliamperes, at a rate of less than or equal to 40 microamperes per second, said increase in intensity being produced by a step up not exceeding 50 microamperes and preferably 30 microamperes;

said electrical signal is applied to the electrodes to treat tension headaches and migraines.

BRIEF DESCRIPTION OF THE DIAGRAMS

FIG. 1, which has already been mentioned, shows a schematic view of the trigeminal nerve and its different branches as well as the corresponding position of the electrode according to the present invention on the upper part of the face.

Figure 2:
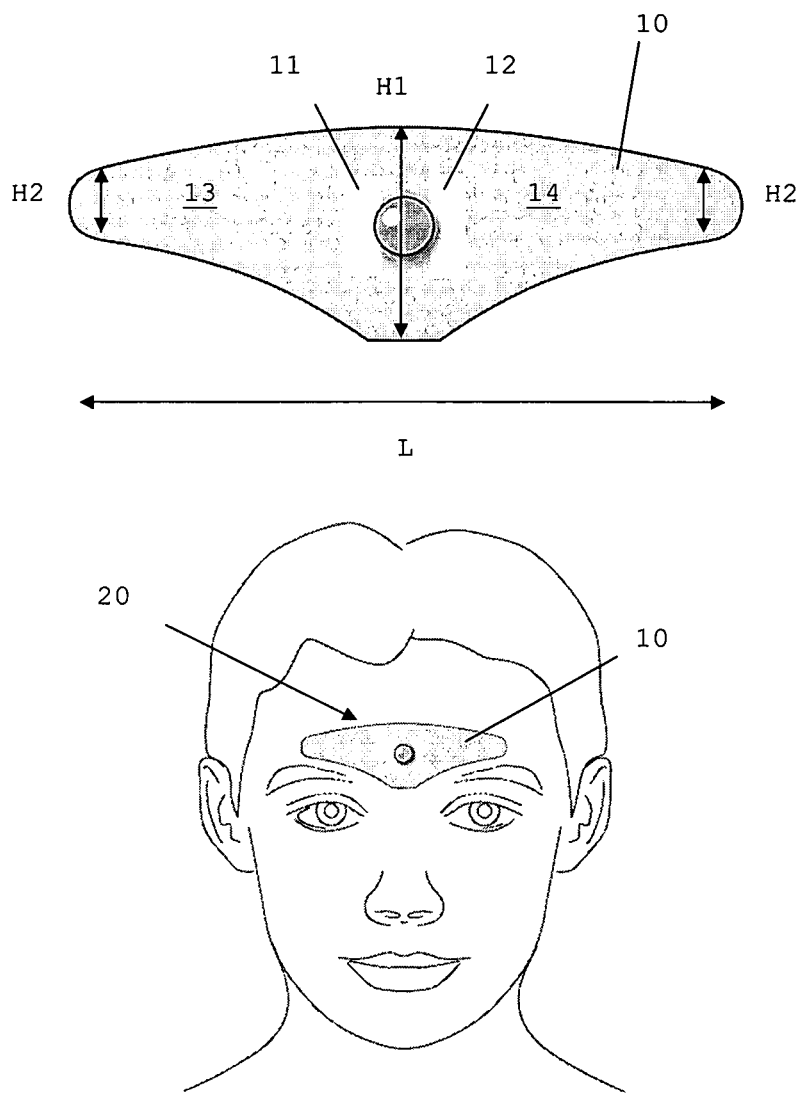

FIG. 2 shows a schematic view of the detail of the shape of the electrode according to the present invention.

DESCRIPTION OF A PREFERRED EMBODIMENT OF THE INVENTION

Reference will be made to the above-mentioned application by the Applicant with regard to the general description of the analgesic electrotherapy device according to the invention, which can also be considered as a way of perfecting the device described in the above-mentioned application.

Thus the device according to the invention, shown in FIG. 2, contains an elongated symmetrical element 10 to support two contact electrodes 11, 12 to be applied transversally on the upper part of the face, in the intraorbital region 20, each of the electrodes 11, 12 being in contact with a self-adhesive conductive gel applied to the surface of the support intended to be applied to the skin of the face. Said conductive gel is applied to two given lateral zones 13, 14, mainly covering the entire support 10, with the exception of an insulating central zone (not shown). The device also contains an electric circuit for supplying said electrodes 11, 12 by means of low-voltage electric pulses.

According to the invention, as shown in FIG. 1, the electrode support 10 is of a size selected so as to allow, independently from the subject, the excitation of the afferent paths of the supratrochlear 2 and supraorbital 3 nerves of the ophthalmic branch 1 of the trigeminal nerve.

More precisely, the present invention relates to the four following aspects:
the shape and size of the electrode;
the duration of the rectangular pulse;
the progression of the increase in intensity and
the step up in intensity.

Characteristics of the Electrode

The electrode according to the invention is designed both to be effective and to limit pain. To be effective, it must allow the excitation of the right and left supratrochlear and supraorbital nerves of all patients regardless of the circumference of their cranium. To limit the pain, it must have the smallest possible surface area so as to reduce the excitation of the nerve fibres that sense pain (nociceptive).

The general shape of the electrode 10 is shown schematically in FIG. 2. It is transversally elongated, symmetrical and has a central height higher than the height of the two ends of the electrode.

The dimensions of the electrode 10 are:
a length L of between 70 and 115 mm with an optimum value of 95 mm;
a height of the central part H1 of between 15 and 50 mm with an optimum value of 30 mm;
a height of the outer part H2 of between 5 and 20 mm with an optimum value of 10 mm.

All other shapes and/or size that the person skilled in the art might devise are either ineffective since they do not allow the afferent paths of the target nerves (left and right supraorbital and supratrochlear) to be excited or they generate additional pain.

Characteristic of the Pulses Used

To excite nerve fibres, TENS analgesic electrotherapy normally uses rectangular pulses. In fact, the rectangular form is described in the literature as the most suitable [8, 9].

The scientific literature describes that the duration of the rectangular pulses must be equal or close to the chronaxy of the target nerve fibres, that is, the nerve fibres that must be excited by the pulse. Chronaxy is the minimum duration of application of the electric current with double the minimum intensity (or rheobasis) required to cause excitation. This way the corresponding electrical energy provided to the tissues is minimal [10]. The top-of-the-range material used by the main manufacturer (CefarCompex) of TENS devices also uses a sensor system to measure the chronaxy of the nerve fibres and then to regulate the duration of the rectangular pulses to make them equal to the chronaxy measured. The fact that the electrical energy transmitted is minimal when the duration of the pulse is regulated to a value equal to the chronaxy of the target nerve fibres is described in this way in CefarCompex's manual of theoretical electrotherapy [11].

The target nerve fibres are, in the case of the present invention, the sensory afferent paths of the supraorbital and supratrochlear nerves. The chronaxy of these sensory fibres of type Aβ is between 30 and 100 μs (microseconds) with an average of 50 μs. It is for this reason that most TENS analgesic electrotherapy devices use rectangular pulses with a duration of between 30 and 100 μs and normally of about 50 μs.

The Applicant's laboratory tests have established that these pulse durations were very painful for the patient and it has been discovered that, contrary to what was expected, much longer pulses were much more comfortable for a reason yet unknown.

According to the present invention, suitable pulse durations are therefore between 150 and 450 μs with an optimum of 250 μs, that is to say 3 to 9 times longer than the pulse durations usually used in TENS analgesic electrotherapy devices in accordance with the state of the art.

Profile of the Increase in Intensity

It is known that the intensity that must be achieved to effectively excite the sensory afferent paths of the supraorbital and supratrochlear nerves lies between 8 and 18 mA (milliamperes). The regulation of the intensities is normally done with TENS devices in a few minutes. In the region that interests us, this increase in intensity is painful, which makes it difficult, indeed impossible to reach the effective intensity of treatment located between 8 and 18 mA.

The nervous system gets used to a given sensation by modifying its threshold of pain perception. This is the mechanism of tolerance. By making use of the phenomenon of tolerance, it is possible to very gradually increase the intensity without producing pain. It is a matter of letting the nervous system raise its threshold of perception of pain before increasing the intensity very slightly and in a manner that remains below the pain threshold. And so on as the nervous system modifies its pain perception threshold.

The above-mentioned laboratory tests have established that the gradient of the increase in intensity that is able to prevent a painful sensation by exploiting the mechanism of tolerance must lie below a value of 17 mA in 7 minutes, that is to say a speed of increase in intensity equal to or less than 40 μA/s (microamperes per second).

This is true as long as the step up in intensity is also adjusted (see below). Steeper gradients of increase in intensity than that mentioned above will cause pain whereas more gradual gradients will be tolerated.

Value of the Step Up in Intensity

The increase in intensity is produced in steps. The step depends on the electronic system that generates the pulses. If the step up in intensity from one pulse to the next is too high, the subject perceives this sudden increase in intensity and therefore pain.

The above-mentioned laboratory tests have established that the value of the step up in intensity from one pulse to the next must not exceed 50 μA, with an optimum of 30 μA.

When the step up in intensity from one pulse to the next is less than 50 μA, the subject does not therefore perceive a sudden increase in intensity and does not feel pain.

BIBLIOGRAPHY (1) Melzack, R, Wall, P, *Pain mechanisms: A new theory*, Science 150: 971-979, 1965;
(2) Wall, P D, Sweet, W H, *Temporary abolition of pain in man*, Science 155: 108-109, 1967;
(3) Woolf, C J, Mitchell, D, Barrett, G D, *Antinociceptive effect of peripheral segmental electrical stimulation in the rat*, Pain 8: 237-252, 1980.
(4) Ahmed H E, White P F, Craig W F, et al., *Use of percutaneous electrical nerve stimulation (PENS) in the short-term management of headache*, Headache April 2000; 40(4): 311-5.
(5) Farina S, Granella F, Malferrari G, Manzoni G C, *Headache and cervical spine disorders: classification and treatment with transcutaneous electrical nerve stimulation*, Headache September 1986; 26(8): 431-3.
(6) Solomon S, Guglielmo K M, *Treatment of headache by transcutaneous electrical stimulation*, Headache 1985; 25(1): 12-5.
(7) Allais G, De Lorenzo C, Quirico P E, Lupi G, Airola G, Mana O, Benedetto C., *Non-pharmacological approaches to chronic headaches: transcutaneous electrical nerve stimulation, lasertherapy and acupuncture in transformed migraine treatment*, Neurol Sci. 24, Suppl 2 (2003): 138-42.
(8): Gad Alon; *Chapter 3: Principles of electrical stimulation*, in Clinical Electrotherapy; Appleton & Lange 1987; pp 29-47.
(9): *Instrumentation for Neuromuscular electrical stimulation*, Snyder-Mackler L, Robinson A J, eds.; Clinical Electrophysiology; Baltimore, Md.; Williams & Wilkins; 1989: 99.
(10): *Instrumentation for Neuromuscular electrical stimulation*, Snyder-Mackler L, Robinson A J, eds.; Clinical Electrophysiology; Baltimore, Md.; Williams & Wilkins; 1989: 100.
(11): *Principes Fondamentaux de l'électrostimulation*, Medi-Compex 1994; Courant optimal; Durée de l'impulsion électrique rectangulaire, pp. 1.2.3 to 1.2.5.

The invention claimed is:

1. Therapeutic method of treatment of headaches, such as tension headaches and migraines, by a device for the electrotherapeutic treatment of headaches such as tension headaches and migraines, the device comprising an elongated symmetrical element to support two contact electrodes to be applied transversally to the upper part of the face, in the intraorbital region, each of the electrodes being in contact with a self-adhesive conductive gel applied to the surface of the support intended to be applied to the skin of the face, the conductive gel being applied to two given lateral zones mainly covering the entire support with the exception of an insulating central zone, as well as an electric circuit for supplying the electrodes by low voltage electric pulses, the electrode support having a length or lateral extension of between 2.75 and 4.5 inches (70 and 115) mm; and the electrode support having a central part with a height of between 0.6 and 2 inches (15 and 50 mm) and outer parts with a height between 0.2 and 0.8 inches (5 and 20 mm) and a shape so as to allow, independently from the subject, the excitation of afferent paths of the supratrochlear and supraorbital nerves of the ophthalmic branch of the trigeminal nerve, the electric circuit including a programmable signal generator suitable for creating pulses of a duration of between 150 and 450 microseconds with a maximum increase in intensity of 0 to 20 milliamperes at a rate of less than or equal to 40 microamperes per second and with a step up in intensity not exceeding 50 microamperes; the method comprising:
  placing the self-adhesive electrode support on the upper part of the face in the intraorbital region so as to cover, on each side, the afferent paths of the supratrochlear and supraorbital nerves of the ophthalmic branch of the trigeminal nerve;
  generating an electrical signal by the programmable signal generator comprising rectangular pulses with a duration of between 150 and 450 microseconds, with a maximum increase in intensity of 0 to 20 milliamperes, at a rate of less than or equal to 40 microamperes per second, said increase in intensity being produced with a step up not exceeding 50 microamperes;
  applying said electrical signal to the electrodes to provide direct stimulation of the supratrochlear or supraorbital nerves to treat tension headaches and migraines.

2. Therapeutic method of treatment of headaches, such as tension headaches and migraines, by a device for the electrotherapeutic treatment of headaches such as tension headaches and migraines, the device comprising an elongated symmetrical element to support two contact electrodes to be applied transversally to the upper part of the face, in the intraorbital region, each of the electrodes being in contact with a self-adhesive conductive gel applied to the surface of the support intended to be applied to the skin of the face, the conductive gel being applied to two given lateral zones mainly covering the entire support with the exception of an insulating central zone, as well as an electric circuit for supplying the electrodes by low voltage electric pulses, the electrode support having a length or lateral extension of between 2.75 and 4.5 inches (70 and 115) mm; and the electrode support having a central part with a height of between 0.6 and 2 inches (15 and 50 mm) and outer parts with a height between 0.2 and 0.8 inches (5 and 20 mm) and a shape so as to allow, independently from the subject, the excitation of afferent paths of the supratrochlear and supraorbital nerves of the ophthalmic branch of the trigeminal nerve, the electric circuit including a programmable signal generator suitable for creating pulses of a duration of between 150 and 450 microseconds with a maximum increase in intensity of 0 to 20 milliamperes at a rate of less than or equal to 40 microamperes per second and with a step up in intensity not exceeding 50 microamperes; the method comprising:
  placing the self-adhesive electrode support on the upper part of the face in the intraorbital region so as to cover, on each side, the afferent paths of the supratrochlear and supraorbital nerves of the ophthalmic branch of the trigeminal nerve;
  generating an electrical signal by the programmable signal generator comprising rectangular pulses with a duration of between 150 and preferably 250 microseconds, with a maximum increase in intensity of 0 to 20 milliamperes, at a rate of less than or equal to 40 microamperes per second, said increase in intensity being produced with a step up not exceeding 50 microamperes;
  applying said electrical signal to the electrodes to provide direct stimulation of the supratrochlear or supraorbital nerves to treat tension headaches and migraines.

3. Therapeutic method of treatment of headaches, such as tension headaches and migraines, by a device for the electrotherapeutic treatment of headaches such as tension headaches and migraines, the device comprising an elongated symmetrical element to support two contact electrodes to be applied transversally to the upper part of the face, in the intraorbital region, each of the electrodes being in contact with a self-adhesive conductive gel applied to the surface of the support intended to be applied to the skin of the face, the conductive gel being applied to two given lateral zones mainly covering the entire support with the exception of an insulating central zone, as well as an electric circuit for supplying the electrodes by low voltage electric pulses, the electrode support having a length or lateral extension of between 2.75 and 4.5 inches (70 and 115) mm; and the electrode support having a central part with a height of between 0.6 and 2 inches (15 and 50 mm) and outer parts with a height between 0.2 and 0.8 inches (5 and 20 mm) and a shape so as to allow, independently from the subject, the excitation of afferent paths of the supratrochlear and supraorbital nerves of the ophthalmic branch of the trigeminal nerve, the electric circuit including a programmable signal generator suitable for creating pulses of a duration of between 150 and 450 microseconds with a maximum increase in intensity of 0 to 20 milliamperes at a rate of less than or equal to 40 microamperes per second and with a step up in intensity not exceeding 50 microamperes; the method comprising:
  placing the self-adhesive electrode support on the upper part of the face in the intraorbital region so as to cover, on each side, the afferent paths of the supratrochlear and supraorbital nerves of the ophthalmic branch of the trigeminal nerve;
  generating an electrical signal by the programmable signal generator comprising rectangular pulses with a duration of between 150 and 450 microseconds, with a maximum increase in intensity of 0 to 20 milliamperes, at a rate of less than or equal to 40 microamperes per second, said increase in intensity being produced with a step up not exceeding 30 microamperes and preferably 30 microamperes;
  applying said electrical signal to the electrodes to provide direct stimulation of the supratrochlear or supraorbital nerves to treat tension headaches and migraines.

4. Therapeutic method of treatment of headaches, such as tension headaches and migraines, by a device for the electrotherapeutic treatment of headaches such as tension headaches and migraines, the device comprising an elongated symmetrical element to support two contact electrodes to be applied transversally to the upper part of the face, in the intraorbital region, each of the electrodes being in contact with a self-adhesive conductive gel applied to the surface of the support intended to be applied to the skin of the face, the conductive gel being applied to two given lateral zones mainly covering the entire support with the exception of an insulating central zone, as well as an electric circuit for supplying the electrodes by low voltage electric pulses, the electrode support having a length or lateral extension of between 2.75 and 4.5 inches (70 and 115) mm; and the electrode support having a central part with a height of between 0.6 and 2 inches (15 and 50 mm) and outer parts with a height between 0.2 and 0.8 inches (5 and 20 mm) and a shape so as to allow, independently from the subject, the excitation of afferent paths of the supratrochlear and supraorbital nerves of the ophthalmic branch of the trigeminal nerve, the electric circuit including a programmable signal generator suitable for creating pulses of a duration of between 150 and 450 microseconds with a maximum increase in intensity of 0 to 20 milliamperes at a rate of less than or equal to 40 microamperes per second and with a step up in intensity not exceeding 50 microamperes; the method comprising:
  placing the self-adhesive electrode support on the upper part of the face in the intraorbital region so as to cover, on each side, the afferent paths of the supratrochlear and supraorbital nerves of the ophthalmic branch of the trigeminal nerve;

generating an electrical signal by the programmable signal generator comprising rectangular pulses with a duration of between 150 and 250 microseconds, with a maximum increase in intensity of 0 to 20 milliamperes, at a rate of less than or equal to 40 microamperes per second, said increase in intensity being produced with a step up not exceeding preferably 30 microamperes;

applying said electrical signal to the electrodes to provide direct stimulation of the supratrochlear or supraorbital nerves to treat tension headaches and migraines.

\* \* \* \* \*